United States Patent
Ruiz et al.

(10) Patent No.: US 9,605,244 B2
(45) Date of Patent: *Mar. 28, 2017

(54) METHOD OF DIFFERENTIATING MAMMALIAN PROGENITOR CELLS INTO INSULIN PRODUCING PANCREATIC ISLET CELLS

(71) Applicant: Vesta Therapeutics Inc., Bethesda, MD (US)

(72) Inventors: Joseph Charles Ruiz, Cary, NC (US); Steven Michael Hoynowski, Durham, NC (US)

(73) Assignee: VESTA THERAPEUTICS INC., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/530,251

(22) Filed: Oct. 31, 2014

(65) Prior Publication Data

US 2015/0056647 A1    Feb. 26, 2015

Related U.S. Application Data

(63) Continuation of application No. 12/470,247, filed on May 21, 2009, now Pat. No. 8,877,497.

(60) Provisional application No. 61/055,341, filed on May 22, 2008.

(51) Int. Cl.
  C12N 5/00    (2006.01)
  C12N 5/071   (2010.01)

(52) U.S. Cl.
  CPC .......... *C12N 5/0676* (2013.01); *C12N 5/067* (2013.01); *C12N 2500/36* (2013.01); *C12N 2500/90* (2013.01); *C12N 2501/065* (2013.01); *C12N 2506/02* (2013.01); *C12N 2506/14* (2013.01); *C12N 2509/00* (2013.01)

(58) Field of Classification Search
  None
  See application file for complete search history.

(56) References Cited

U.S. PATENT DOCUMENTS

| | | | |
|---|---|---|---|
| 5,919,702 A | 7/1999 | Purchio et al. | |
| 6,069,005 A | 5/2000 | Reid et al. | |
| 6,153,432 A | 11/2000 | Halvorsen et al. | |
| 6,391,297 B1 | 5/2002 | Halvorsen | |
| 6,429,013 B1 | 8/2002 | Halvorsen et al. | |
| 6,555,374 B1 | 4/2003 | Gimble et al. | |
| 6,610,535 B1 | 8/2003 | Lu et al. | |
| 6,841,150 B2 | 1/2005 | Halvorsen et al. | |
| 7,001,746 B1 | 2/2006 | Halvorsen et al. | |
| 7,033,587 B2 | 4/2006 | Halvorsen et al. | |
| 7,413,897 B2 | 8/2008 | Reid et al. | |
| 7,456,017 B2 | 11/2008 | Kubota et al. | |
| 8,877,497 B2* | 11/2014 | Ruiz | C12N 5/0676 435/375 |
| 2002/0182188 A1 | 12/2002 | Reid et al. | |
| 2004/0136967 A1 | 7/2004 | Weiss et al. | |
| 2005/0053588 A1 | 3/2005 | Yin | |
| 2007/0155009 A1 | 7/2007 | McClelland et al. | |
| 2007/0254359 A1 | 11/2007 | Rezania et al. | |
| 2008/0019949 A1 | 1/2008 | Mitchell et al. | |
| 2008/0063628 A1 | 3/2008 | Davis et al. | |

FOREIGN PATENT DOCUMENTS

| WO | WO-03/050249 A2 | 6/2003 |
| WO | WO-03/103613 A2 | 12/2003 |
| WO | WO-2006/045331 A1 | 5/2006 |

OTHER PUBLICATIONS

Yang et al. PNAS 2002;99:8078-83.*
Ren et al. J Cell Biochem 2010;109:236-44.*
Assady, et al. "Insulin Production by Human Embryonic Stem Cells" Diabetes, Aug. 2001, vol. 50, pp. 1691-1697.
Goicoa, et al. "Sodium Butyrate Activates Genes of Early Pancreatic Development in Embryonic Stem Cells" Cloning and Stem Cells, 2006, vol. 8, No. 3, pp. 140-149.
International Search Report (PCT/US2009/044856) dated Sep. 17, 2009.
Jiang J et al: "Generation of insulin-producing islet-like clusters from human embryonic stem cells", Stem Cells, vol. 25, No. 8, Aug. 1, 2007 (Aug. 1, 2007), pp. 1940-1953, XP008084029.
Jiang Wei et al: "In vitro derivation of functional insulin-producing cells from human embryonic stem cells", Cell Research, vol. 17, No. 4, Apr. 10, 2007 (Apr. 10, 2007), pp. 333-344, XP002455184.
Kubota, et al. "Clonogenic hepatoblasts, common precursors for hepatocytic and biliary lineages, are lacking classical major histocompatibility complex class I antigen" PNAS, Oct. 24, 2000, vol. 97, No. 22, pp. 12132-12137.
Li, et al. "Combination of GLP-1 and Sodium Butyrate Promote Differentiation of Pancreatic Progenitor Cells Into Insulin-Producing Cells" Tissue & Cell, 2008, vol. 40, pp. 437-445.
Notice of Allowance on U.S. Appl. No. 12/740,247 dated Jul. 8, 2014.
Office Action mailed Nov. 8, 2012 in European Application No. 09751581.1.
Tsuchiya, et al., Long-term Expansion of Mouse Hepatic Stem/Progenitor Cells in a Novel Serum-Free Culture System, Gastroenterology 2005:128:2089-2105.
US Office Action on U.S. Appl. No. 12/470,247 dated Dec. 13, 2011.
US Office Action on U.S. Appl. No. 12/470,247 dated Aug. 7, 2012.
Yamada et al., "Differentiation of Adult Hepatic Stem-Like Cells Into Pancreatic Endocrine Cells", Cell Transplantation 2005, vol. 14, No. 9, pp. 647-653.

* cited by examiner

*Primary Examiner* — Janice Li
(74) *Attorney, Agent, or Firm* — Gilberto M. Villacorta; Natasha Iyer; Foley & Lardner LLP

(57) ABSTRACT

The invention relates to methods for differentiating progenitor cells into insulin producing pancreatic islet cells and compositions and methods for using such cells.

5 Claims, 2 Drawing Sheets

Lane 1: Pdx
Lane 2: insulin
Lane 3: glucagon
Lane 4: somatostatin
Lane 5: glut2
Lane 6: GADPH (control)

METHOD OF DIFFERENTIATING MAMMALIAN PROGENITOR CELLS INTO INSULIN PRODUCING PANCREATIC ISLET CELLS

CROSS-REFERENCE TO RELATED APPLICATIONS

This application is a continuation of U.S. patent application Ser. No. 12/470,247, filed May 21, 2009, now U.S. Pat. No. 8,877,497, which claims priority from U.S. Provisional Patent Application No. 61/055,341, filed May 22, 2008. The entire disclosures of which are incorporated herein by reference.

FIELD OF THE INVENTION

The present invention relates generally to the differentiation of mammalian progenitor cells of a particular cell type into another cell type. More specifically, the present invention relates to a method of differentiating mammalian progenitor cells, including stem cells, into insulin producing pancreatic islet cells.

BACKGROUND OF THE INVENTION

Diabetes mellitus ("diabetes") is one of the leading causes of morbidity and mortality in the United States. Patients suffering from diabetes have metabolism disorder(s) and abnormally elevated blood sugar levels (i.e., hyperglycemia), which results from low levels of insulin production.

Beta cells found in the islets of Langerhans in the pancreas ("pancreatic islet β cells) produce insulin. In Type I and (to a lesser extent) Type II diabetes, a deficiency in insulin production can be attributed to inadequate mass of functional insulin-producing islet cells. The cause of this cell loss may be viral, chemical, and/or autoimmune attack and destruction of the cells.

Given this etiology, attempts have been made to reverse or prevent the onset of diabetes by replenishing the lost or damages cells with donor pancreatic cells. While cell-based therapies of this sort have shown promise, the supply of pancreatic cells, particularly human pancreatic cells, is in perpetual short supply, both in terms of quantity and quality, for research and/or transplantation. The present invention provides a method to increase this short supply, in part, by enabling the use of progenitor cells from any tissue, including non-pancreatic tissue, to arrive at insulin-producing pancreatic cells.

SUMMARY OF THE INVENTION

The present invention provides a method for differentiating progenitor cells into insulin-producing pancreatic cells, the method comprising: (a) incubating the progenitor cells in serum-free pre-induction media comprising 2 mmol/L sodium butyrate; and, subsequently, (b) incubating the progenitor cell in induction media comprising knock-out replacement serum; and for a time sufficient to differentiate the progenitor cells into insulin producing pancreatic cells. The progenitor cells may be hepatic stem cells, umbilical cord matrix stem cells, or adipose stem cells. Preferably, the progenitor cells are derived from human tissue. The induction media may further comprise about 2% knock-out replacement serum.

Another embodiment of the invention provides a method for evaluating the toxicity of a compound in vitro, comprising contacting a pancreatic β islet-like cell differentiated from progenitor cells according to the invention with said compound; and measuring the viability of said pancreatic β islet-like cell, wherein a decrease in viability in the presence of said compound compared to that in the absence of said compound indicates that said compound is toxic in vivo.

Yet another embodiment of the invention provides a method for evaluating the activity of a compound in vitro, comprising contacting a metabolically active pancreatic β islet-like cell differentiated from progenitor cells according to the invention with said compound; and measuring the metabolic activity of said pancreatic β islet-like cell, wherein a decrease or increase in metabolic activity in the presence of said compound compared to that in the absence of said compound indicates that said compound has activity in vivo.

A still further embodiment of the invention provides a method for treating loss or depletion of β islet cell in the pancreas of an individual in need thereof comprising administering to the individual a population of pancreatic β islet-like cells differentiated from umbilical cord matrix cells according to the invention. The patient may be diagnosed with diabetes.

A still yet further embodiment of the invention provides a drug screening kit comprising a panel of pancreatic β islet-like cells of the invention and at least one reagent for measuring insulin production and/or gene expression. In one embodiment, the kit comprises at least one medium for culturing the progenitor-derived pancreatic β islet-like cells.

DETAILED DESCRIPTION OF THE INVENTION

Figure 1:
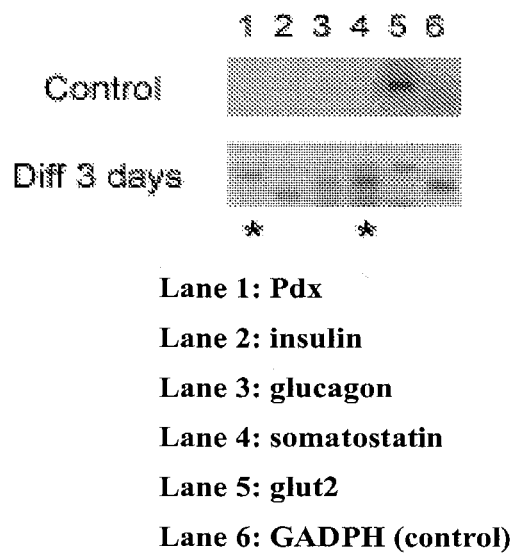
FIG. 1 provides the results of a PCR analysis of cDNA taken from human hepatic stem cells that have been differentiated into pancreatic β islet-like cells in accordance with the present invention. Lane 1 (Pdx), lane 2 (insulin), lane 3 (glucagon), lane 4 (somatostatin), lane 5 (glut2), lane 6 (GADPH, control).

The present invention provides a method of differentiating progenitor cells from pancreatic or non-pancreatic tissue into insulin-producing pancreatic cells. Progenitor cells of any tissue, including adipose progenitor cells, hepatic progenitor cells, and umbilical matrix progenitor cells, may be induced to differentiate into insulin-producing pancreatic cells by using the teachings of the present invention.

The term "progenitor" cell is used broadly herein to define any cell that has the capacity to differentiate into a more "mature" cell. Hence, the term "differentiate" refers not only to the "maturation" of a cell within a single cell-type/lineage (e.g., hepatic stem cell to hepatoblast), but alternatively, also to the "conversion" of a cell from one type/lineage to another (e.g., hepatic cell to pancreatic cell).

By way of example, the term "hepatic progenitors," as used herein, is broadly defined to include any cell that is not a fully mature (i.e., differentiated) hepatocyte or biliary cell. Hence, "hepatic progenitors" encompasses both hepatic stem cells and their progeny immature progeny. "Progeny" may include both self-replicating hepatic stem cells, hepatoblasts, bipotent progenitors therefrom, and progenitors committed to differentiate into a particular cell type (e.g., a committed biliary cell progenitor or hepatocyte). According to the present invention, a hepatic progenitor can also "differentiate" into a pancreatic cell.

While most, if not all, of the discussion and examples of progenitors herein will be with reference to human-derived cell populations (both adult and fetal), the teachings herein should not be limited to humans. In fact, one of ordinary skill in the art may be expected to apply the teachings herein to the isolation and differentiation of progenitors from mammals, generally (e.g., mice, rats, dogs, etc.) Accordingly, the scope of the present invention is intended to include progenitors of any and all mammals.

Hepatic Progenitor Cells

Each of the aforementioned populations of hepatic progenitor cells (e.g., "stem cells," "hepatoblasts," or "hepatocytes") can be identified by their respective size and/or specific arrangement of markers unique to the respective populations. See Table 1, below.

|  | Hepatic Stem Cells | Hepatoblasts | Adult Hepatocytes (Adult Biliary Cells) |
|---|---|---|---|
| Size (μM) | 7-9 | 10-12 | 17-25 |
| EpCAM | +++ | ++ | -- (++) |
| AFP | --- | +++ | -- (--) |
| Albumin | + | ++ | +++ (--) |
| CK19 | +++ | ++ | -- (++) |
| Claudin 3 | +++ | - | - (+) |
| Telomerase | +++ | +++ | ++ (n.t) |
| Sonic and Indian Hedgehog | +++ | ++ | -- (--) |
| 1-CAM1 | --- | +++ | ++ (+) |
| N-CAM | +++ | --- | -- (--) |
| MDR3 | - | - | -- (+++) |
| P450-3A4 | --- | --- | +++ (--) |

EpCAM—epithelial cell adhesion molecule;
CKI9 = cytokeratin 19, a biliary specific cytokeratin;
I-CAM = intercellular adhesion molecule;
NCAM—neuronal cell adhesion molecule;
MDR3 = muldrug resistance gene isoform 3 (involved in bile transport)
P450-C3A4 = cytochrome P450 3A4;
Claudin 3 = tight junction protein (isoform 3)

Hepatic stem cells (HSCs) are pluripotent cells found in the ductal plates (also called limiting plates) in fetal and neonatal livers and in the Canals of Hering in pediatric and adult livers and showing evidence of self-replication with expression of telomerase and being capable of forming mature liver cells when transplanted. These cells are EpCAM+, NCAM+, ALB+, CK8/18+, CK19+, CD133/1+, and are negative for all hemopoietic markers tested (e.g., CD34, CD38, CD45, CD14), mesenchymal cell markers (CD146, VEGFr, CD31) and for expression of P450s or alpha-fetoprotein. The HSCs have been found to give rise to hepatoblasts and to committed (unipotent) biliary progenitors.

Hepatoblasts (HBs) are pluripotent cells found throughout the parenchyma of fetal and neonatal livers and as single cells or small aggregates of cells tethered to the ends of the Canals of Hering. HBs derive from the HSCs. HBs share many antigens present on HSCs but with important distinctions. For example, HBs do not express NCAM but rather ICAM1 and they express significant amounts of alpha-fetoprotein and fetal forms of P450s. These HBs give rise to the unipotent progenitors, the committed hepatocytic and biliary progenitors.

Hepatic Committed Progenitors are unipotent progenitors of either the hepatocytic and biliary lineages. Their antigenic profile overlaps with that of the HBs; however, biliary committed progenitors express CK19 but not AFP or ALB, whereas the hepatocytic committed progenitors express AFP and ALB but not CK19. Committed biliary progenitors derive directly from hepatic stem cells and also from hepatoblasts.

Mesenchymal Cells (MCs) include cells at various lineage stages of the many different mesenchymal cell types (listed as the mature cells and, in parentheses, their precursors): including stroma (mesenchymal stem cells), endothelia (angioblasts), stellate cells (stellate cell precursors), and various hemopoietic cells (hemopoietic stem cells)

Isolation of Hepatic Progenitor Cells

Hepatic progenitors suitable for in vitro isolation and differentiation in accordance with the instant invention are not limited to those isolated or identified by any particular method. By way of example, methods for the isolation and identification of the hepatic progenitors have been described in, for example, U.S. Pat. No. 6,069,005 and U.S. patent application Ser. Nos. 09/487,318; 10/135,700; 10/387,547 and 11/560,049 the disclosures of which are incorporated herein in their entirety by reference.

Hepatic stem cells and hepatoblasts have characteristic antigenic profiles and can be isolated by protocols described previously. For example, hepatic stem cells and hepatoblasts share numerous antigens (e.g., cytokeratins 8, 18, and 19, albumin, CD133/1, and epithelial cell adhesion molecule ("EpCAM") and are negative for hemopoietic markers (e.g., glycophorin A, CD34, CD38, CD45, CD14) and mesenchymal cell markers (e.g., CD146, CD31, VEGFr or KDR).

Alternatively, hepatic stem cells and hepatoblasts can be distinguished from each other by size (the stem cells are 7-9 μm; the hepatoblasts are 10-12 μm), by morphology in cultures (the stem cells form dense, morphologically uniform colonies, whereas the hepatoblasts form cord-like structures interspersed by clear channels, presumptive canaliculi), by distinctions in the pattern of expression of certain antigens (EpCAM is expressed throughout the hepatic stem cells but is confined to the cell surface in the hepatoblasts), or by distinct antigenic profiles (N-CAM is present in the hepatic stem cells, whereas alpha-fetoprotein (AFP) and ICAM1 are expressed by the hepatoblasts).

In one embodiment, primary hepatic stem cells are obtained from human livers in a manner described above. Briefly, a single cell suspension of whole liver hepatic cells is obtained and plated onto tissue culture plastic, alone, or on a matrix of extracellular proteins comprising collagen and laminin. The cells are then incubated in media comprising serum for a time necessary for the suspended cells to adhere to the plate (usually, 1-2 days).

Thereupon, the serum-containing media is removed and replaced with "Hiroshi Kubota's Media," (HK), which is serum-free, and supplemented with specific growth factors. More specifically, HK is a serum-free basal medium (e.g., RPMI 1640) containing no copper, low calcium (<0.5 mM) and supplemented with insulin (5 µg/ml), transferrin/fe (5 µg/ml), high density lipoprotein (10 µg/ml), selenium (10-10 M), zinc (10-12 M) and 7.6 µE of a mixture of free fatty acids bound to purified albumin. The detailed methods for the preparation of this media have been published elsewhere, e.g., Kubota H, Reid L M, Proceedings of the National Academy of Sciences (USA) 2000; 97:12132-12137, the disclosure of which is incorporated herein in its entirety by reference.

Under these conditions, over a period of 5-14 days, colonies of hepatic stem cells form relatively rapidly on the plate.

Umbilical Cord Matrix Progenitor Cells

Umbilical cord matrix (UCM) progenitor cells can be isolated using any technique known in the art, such as described in U.S. Pat. No. 5,919,702, and US Patent Application Publication Nos. 20040136967 and 20080019949, all of which disclosures are incorporated herein in their entirety by reference. UCM cells (also known as Wharton's Jelly Cells), can be found in nearly any animal with an umbilical cord and obtained from Wharton's jelly collected therein. It may be advantageous to obtain UCM stem cells from Wharton's jelly obtained from an umbilical cord associated with a developing fetus or neonate, because of the "fetal" nature of cells, which can minimize any immune rejection of the cells and/or the insulin-producing pancreatic cells differentiated therefrom. As a result, such cells may be useful as "ubiquitous donor cells" for the production of pancreatic islet cells or beta-like cells for use in any subject in need thereof.

Whole UCM cells are isolated from umbilical cord and added to a medium which contains factors that stimulate UCM cell growth without differentiation and allows, when cultured, for the selective adherence of the UCM stem cells to a substrate surface. The specimen-medium mixture is cultured and the non-adherent matter is removed from the substrate surface. Any appropriate type of culture medium can be used to isolate the UCM cells of the invention, and the culture medium may be supplemented with one or more components including, for example, serum.

After culturing the cells for a sufficient period of time, for example, about 10-12 days, UCM derived stem cells present in the explanted tissue will tend to have grown out from the tissue, either as a result of migration therefrom or cell division or both. These UCM derived stem cells may then be removed to a separate culture vessel containing fresh medium of the same or a different type as that used initially, where the population of UCM derived stem cells can be mitotically expanded.

In one embodiment for culturing UCM derived stem cells, umbilical cord tissue sections are placed in a tissue culture dish containing glass slides on the bottom of the dish and cultured in Dulbecco's MEM plus 20% FBS; or RPMI 1640 containing 10% FBS, 5% embryonic stem cell qualified FBS and antimicrobial compounds. The tissue is preferably incubated at 37-39° C. and 5% $CO_2$ for 10-12 days.

In another embodiment, umbilical cord completely dissected and cleaned of blood is enzymatically (e.g., with a solution of 40 U/mL hyaluronidase and 0.4 mg/mL collagenase) and mechanically (e.g., with a pestle an 40 mesh screen) digested. The single cell suspension thus obtained is suspended in Defined Media (DM), which contains 58% low glucose DMEM, 40% MCDB201 (Sigma, St. Louis, Mo.), 1× insulin-transferrin-selenium-A (Invitrogen, Carlsbad, Calif.), 0.15 mg/mL AlbuMAX I (Invitrogen, Carlsbad, Calif.), 1 nM dexamethasone, 100 uM ascorbic acid 2-phosphate, 100 U penicillin, 1000 U streptomycin, 2% FBS, 10 ng/mL EGF, and 10 ng/mL platelet-derived growth factor BB (PDGF-BB). The cells are then seeded and expanded in DM.

The invention contemplates that once stem cells have been established in culture, their ability to serve as progenitors for mature cells or cell lines can be maintained, for example, by regular passage to fresh medium as the cell culture reaches an appropriate density or percentage of confluency, or by treatment with an appropriate growth factors, or by modification of the culture medium or culture protocol, or by some combination of the above.

Adipose Stem Cells

Methods of deriving adipose stem cells (ASCs) from adipose tissue are presented in U.S. Pat. Nos. 6,153,432, 6,391,297, 6,429,013, 6,555,374, 6,841,150, 7,001,746 and 7,033,587, the disclosures of which are incorporated herein in their entirety by reference. Briefly, in one example, once the tissue is procured, it is subjected to differential centrifugation and expanded in culture. A single gram of tissue typically yields between 50,000 to 100,000 stem cells within 24 hours of culture. Expansion media preferably comprises 60% DMEM (low glucose) and 40% MCDB-201 supplemented with 10% fetal bovine serum (FBS); 5 µm/ml insulin, 5 µm/ml transferrin and 5 ng/ml selenium; $10^{-9}$ M dexamethasone; 10 ng/ml epidermal growth factor (EGF); $10^{-4}$ M ascorbic acid 2-phosphate; 100 U/ml penicillin; and 100 U/ml streptomycin. Without being held to or bound by theory, it is believed that the addition of EGF to the media enhances the ability of the ASCs to later differentiate into insulin-producing islet cells. Ascorbic acid 2-phosphate may have a similar effect upon ASCs.

Differentiation of Progenitor Cells into Insulin-Producing Pancreatic Cells

The terms "pancreatic islet β-like" cell or "insulin-producing pancreatic islet" cell as used herein refer to cells that express at least two markers indicative of a pancreatic islet β cell. Illustrative pancreatic islet β cell markers include, but are not limited to, expression of pancreas duodenum homeobox-1 (PDX-1), insulin, somatostatin, glucose transporter-2 (glut2), glycogen, amylase, and neurogenin 3 (Ngn3). Further illustrative markers include morphological characteristics such as a spherical shape. Yet further illustrative markers include characteristics such as insulin production. Thus, in certain embodiments, the pancreatic islet b-like cells express more mature pancreatic islet β cell functions, such as production of insulin.

In certain embodiments, the hepatocyte-like cells of the invention express two or more hepatocyte markers as described herein. In another embodiment, the pancreatic islet β-like cells express three or more of the pancreatic islet β cell markers as described herein. In certain embodiments, the pancreatic islet β-like cells of the invention express five, six, seven, eight, nine, ten or more hepatocyte markers as described herein. As would be appreciated by the skilled artisan, the pancreatic islet β-like cells of the invention may also express other known markers or functions.

In one embodiment, the progenitor cells are differentiated using the following method: Prior to induction, the progenitor cells are cultured for a time sufficient for them to adhere to the tissue culture plate in Defined Media containing:

0.5-10 g/L low (preferably, 1 g/L) glucose DMEM, MCDB201 pH 7.4, 1× Insulin-Transferrin-Selenium (ITS, Invitrogen), 0.1-5 mg/mL (preferably, 0.15 mg/mL) albumin (e.g., Albumax, Invitrogen), 0.5-5 nM (preferably, 1 nM) dexamethasone, 25-250 μM (preferably, 100 μM) ascorbic acid-2-phosphate, 5-50 ng/mL (preferably, 10 ng/mL) EGF, 5-50 ng/mL (preferably, 10 ng/mL) PDGF, 1-5% (preferably, 2%) FBS, and Penicillin/Streptomycin (Pen/Strep). The progenitor cells are then cultured for about 24 hours in Pre-induction Media containing: Serum Free Iscove's Modified Dulbecco's Medium (IMDM), 1-5 mM (preferably, 2 mM) sodium butyrate, and Pen/Strep. The cells are then cultured for 3 to 36 hours, but preferably for about 24 or more hours in Differentiation Media containing IMDM, 1-5% (preferably, 2%) Knock-out Replacement Serum (KSR, Gibco), and Pen/Strep.

Sodium butyrate is a potent histone deacetylase inhibitor (HDACI) that modulates the expression of a large number of genes. Other HDACIs suitable for the invention are phenyl butyrate, retinoic acid, valproic acid, APHA Compound 8, Apicidin, (−)-Depudecin, Scriptaid, Sirtinol, and Trichostatin.

In another embodiment, the progenitor cells are differentiated using the following method: Prior to induction, the progenitor cells are cultured for a time sufficient for them to adhere to the tissue culture plate in Defined Media containing: Low (1 g/L) glucose DMEM, MCDB201 pH 7.4, 1× Insulin-Transferrin-Selenium (ITS, Invitrogen), 0.15 g/mL Albumax (Invitrogen), 1 nM Dexamethasone, 100 μM Ascorbic acid-2-Phosphate, 10 ng/mL EGF, 10 ng/mL PDGF, 2% FBS, and Penicillin/Streptomycin (Pen/Strep). The progenitor cells are then cultured for about 24 in Pre-induction Media containing: "low" 1 g/L glucose-DMEM, 5-25 mM (preferably, 10 mM) nicotinamide, 0.5-5 mM (preferably, 1 mM) β-mercaptoethanol, 2% FBS, and Pen/Strep. The cells are then cultured for 10 or more hours in Differentiation Media containing serum-free 1 g/L glucose-DMEM, 10 mmol/L nicotinamide, 1 mmol/L β-mercaptoethanol, and Pen/Strep.

The progenitor cells can be differentiated in the presence of a scaffold to allow three-dimensional culturing of the cells during differentiation. The scaffold material may comprise naturally occurring components or may be comprised of synthetic materials, or both. The scaffold material may also be biocompatible. Illustrative scaffold material includes extracellular matrices and materials described in. Other scaffold materials that can be used in the context of the present invention include but are not limited to one or a mixture of two or more of the following: collagens (e.g., collagen types I, III, IV, V and VI), gelatin, alginate, fibronectin, laminin, entactin/nidogen, tenascin, thrombospondin, SPARC, undulin, proteoglycans, glycosaminoglycans (e.g., hyaluronan, heparan sulfate, chondroitin sulfate, keratan sulfate and dermatan sulfate), polypropylene, TER polymer, alginate-poly L-lysine, chondroitin sulfate, chitosan, MATRIGEL (Becton-Dickinson) or other commercially available extracellular matrix materials.

In one particular embodiment, the extracellular matrix for use in differentiating the UCM into hepatocyte-like cells is collagen I. Collagen coated plates are commercially available from Becton-Dickinson.

The progenitor cells are cultured in one or more of the media described herein for a time sufficient for expression of at least two of the following markers: PDX-1, insulin, somatostatin, glut2, glycogen, amylase, and Ngn3; morphological characteristics such as round shape and insulin production.

In one particular embodiment, the progenitor cells are differentiated into insulin-producing pancreatic islet cells by culturing in IMDM differentiation media comprising 2% KSR and Pen/Strep on a collagen I matrix.

The cells are typically cultured for a sufficient time to acquire pancreatic islet β cell-like functional properties, such as insulin production. In this regard, differentiation is assessed by measuring functional properties such as insulin production, using techniques known in the art. Insulin is small peptide hormone produced solely by b islet cells found in the pancreas and secreted into the blood (in vivo) or media (in vitro). To demonstrate insulin secretion, differentiated cells may be stained with anti-human insulin antibody. Standard ELISA techniques may also be used to detect and quantify the amount of insulin secreted into the media.

Briefly, strips are assembled on microtiter plates and each well filled with 300 μL of HRP wash buffer, and the plates incubated at room temperature for 5 minutes. The buffer is then removed and of 20 μL sample added to the wells with 20 μL of detection antibody. The plates are then again incubated at room temperature for 1 hour on an orbital shaker. The contents of the wells are decanted and washed three times with HRP wash buffer. 100 μL of enzyme solution is added to each well and allowed to incubate for 30 minutes at room temperature on an orbital shaker. Again, the wells are washed 5 times with HRP buffer Next, 100 μL of substrate solution is added to the wells and incubated for 10 minutes at room temperature on an orbital shaker. A blue color typically then develops from a chemical reaction. The reaction is terminated with 100 μL of "stop solution." Solutions are commercially available. The plates are analyzed at 450 nm.

Immunohistochemistry is performed as follows: cells are fixed in methanol or paraformaldehyde for 2 minutes, and subsequently washed with PBS. 3% hydrogen peroxide is added and incubated for 60 minutes. Upon washing the solution, primary antibody at 1:500 dilution in PBS/5% blotto/0.3% Tween is applied and allowed to incubate for 60 minutes. Again, the cells are wash three times with PBS to remove the solution, and secondary antibody at 1:400 dilution in PBS/5% blotto/0.3% Tween is applied for 60 minutes.

As would be recognized by the skilled artisan upon reading the present disclosure, any of a variety of techniques known in the art can be used to determine expression of pancreatic b islet cell markers and cell morphology, including but not limited to gene expression assays such as PCR, RT-PCR, quantitative PCR, protein expression analyses including immunohistochemistry, immunofluorescence assays, and the like. Such techniques are known in the art and need no further elaboration here.

Differentiation of the cells of the invention can be detected by a variety of techniques, such as, but not limited to, flow cytometric methods, immunohistochemistry, immunofluorescence techniques, in situ hybridization, and/or histologic or cellular biologic techniques. According to the present invention, greater than 30% of the progenitor cells can be differentiated into insulin producing pancreatic islet cells, preferably greater than about 50% of the cells, more preferably greater than about 75% of the cells, and most preferably greater than about 90% of the cells.

Methods of Using the Insulin-Producing Pancreatic Cells

The differentiated pancreatic β islet-like cells of the invention may also be provided as a panel of pancreatic β islet-like cells derived from multiple different sources (e.g., umbilical cords, livers) from individuals of diverse genetic backgrounds and even from different animal sources. For example, a panel of UMC-derived pancreatic β islet-like cells may include pancreatic β islet-like cells derived from UMC sources from individuals known to have polymorphisms in genes encoding drug-metabolizing enzymes and drug transporters. The panels of the invention may be provided as part of a drug screening kit including reagents for drug screening, such reagents including, for example, any of the culture media described herein, and reagents for detecting, e.g., insulin expression.

In one embodiment, the pancreatic β islet-like cells of the invention can be genetically modified. In accordance with this embodiment, the pancreatic β islet-like cells of the invention are exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA, such as antisense RNA, siRNA or a ribozyme.

Thus, the coding polynucleotide can encode a gene conferring, for example, resistance to a toxin or an infectious agent, a hormone (such as peptide growth hormones, hormone releasing factor, sex hormones, adrenocorticotrophic hormones, cytokines such as interferons, interleukins, and lymphokines), a cell surface-bound intracellular signaling moiety such as cell-adhesion molecules and hormone receptors, and factors promoting a given lineage of differentiation, or any other transgene with known sequence.

As will be next described, the insulin-producing pancreatic islet cells differentiated from progenitor cells of the invention are useful in a variety of settings, including drug screening, screening for drug interactions, transplantation, tissue/organ regeneration and treatment of liver damage or other liver disorders.

In one embodiment, the invention provides methods for testing the activity of a compound (e.g., a drug or candidate drug). The activity of a compound may be assessed by measuring the effect of the drug on the viability and/or metabolic activity of the pancreatic β islet-like cells of the invention or the effect of the drug on drug transport transporters. As would be understood by the skilled artisan in view of the present disclosure, the pancreatic β islet-like cells of the invention may be used in any known drug screening assay, such as assays on insulin production, current drug screening assays that use islet cells, and the like. The present invention provides the advantage that the pancreatic β islet-like cells of the invention are easily procured and can be derived from diverse tissues from individuals with diverse genetic backgrounds.

In one embodiment, the present invention provides methods for testing the activity (such as the toxicity) of a compound by contacting the pancreatic β islet-like cells of the invention with a compound arid measuring the viability of the pancreatic β islet-like cells. A decrease in viability in the presence of a test compound compared to that in the absence of the test compound indicates that the compound is toxic in vivo. Viability of cells can be determined using techniques well known to the skilled artisan, such as staining followed by flow cytometry or simply by visualizing the cells with a microscope using a hemacytometer.

In another embodiment, the present invention provides methods for testing the activity of a compound by contacting the pancreatic islet-like cells of the invention with a compound and measuring the metabolic activity of the same cells. A decrease or increase in metabolic activity in the presence of a test compound compared to that in the absence of the test compound indicates a drug activity in vivo.

A further embodiment of the invention provides methods for evaluating drug interactions. Drug interactions can be evaluated by contacting the cells of the invention with two compounds and determining whether the effect on the cells of one compound is impacted by the presence of the second compound. For example, the method may comprise contacting a first population of the pancreatic β islet-like cells with a first compound, contacting a second population of the pancreatic β islet-like cells with a second compound and contacting a third population of pancreatic β islet-like cells with both the first and the second compounds and measuring a particular effect in each of the populations (e.g., cell viability, metabolic activity, insulin production) wherein a statistically significant decrease or increase in an effect in the third population contacted with both compounds as compared to either of the first or second populations would indicate a drug interaction. A drug interaction may comprise one drug inhibiting another drug or one drug increasing the activity of another drug.

As would be recognized by the skilled artisan, gene expression can be measured using any of a variety of techniques known in the art, such as but not limited to, quantitative polymerase chain reaction (QC-PCR or QC-RT PCR). Other methods for detecting mRNA expression are well-known and established in the art and may include, but are not limited to, transcription-mediated amplification (TMA), polymerase chain reaction amplification (PCR), reverse-transcription polymerase chain reaction amplification (RT-PCR), ligase chain reaction amplification (LCR), strand displacement amplification (SDA), and nucleic acid sequence based amplification (NASBA).

Measurements of metabolic activity is carried out using techniques known in the art, such as, for example, by contacting the cells with a test compound and collecting supernatant. Metabolites of the compound present in the supernatant are measured using known techniques, such as through an appropriate type of high performance liquid chromatography (HPLC). Thymidine incorporation by cultured cells can be measured to assess cell proliferation in vitro.

The present invention further provides methods for the treatment of damage or disease arising from loss of pancreatic islet-β cells. In this regard, the differentiated insulin producing pancreatic islet cells of the invention can be used for the treatment of any disease arising from loss of pancreatic islet cells, including but not limited to, diabetes, both Type I and Type II.

The present invention provides methods for the treatment of islet cell damage by administering to an individual in need thereof, an effective amount of the differentiated pancreatic β islet-like cells of the invention. By effective amount is meant an amount sufficient to provide a beneficial effect to the individual receiving the treatment, such as an amount to ameliorate symptoms of diabetes to improve liver function. In certain embodiments, an effective amount is an amount sufficient to regrow functioning pancreatic β islet cells. A "therapeutic" treatment is a treatment administered to a subject who exhibits signs of pathology for the purpose of diminishing or eliminating those signs.

In one embodiment, the present invention provides methods for improving or restoring pancreatic insulin production by administering an effective amount of the differentiated pancreatic β islet-like cells of the invention. In this regard, pancreatic β islet-like cells are differentiated using methods as described herein, from progenitors, preferably of an individual patient, for autologous (in situations where appropriate cells may have been harvested and stored at the time of birth) or allogeneic transplantation to a histocompatible recipient according to the methods described herein and practiced in the art.

The cells are cultured as described herein, harvested, and may be introduced into the spleen, circulation, and/or peritoneum of a patient suffering from loss or reduction of insulin production of any origin, secondary to viral infection, toxin ingestion, or inborn metabolic errors, etc. Wherever possible, radiologically guided, minimally invasive methods are used to implant the cells. Cells genetically engineered with genes encoding enzymes designed to improve hepatic function are also contemplated herein.

In one particular embodiment, the pancreatic β islet-like cells of the present invention are administered to an individual undergoing a transplant of p islet cells. The cells of the present invention may be administered either alone, or as a pharmaceutical composition in combination with diluents and/or with other components such as islet cell growth factors (e.g., BMPs, TGF-beta 1, IGF, FGF) or other hormones or cell populations.

Briefly, compositions of the present invention may comprise a pancreatic β islet-like cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention may formulated for intravenous or parenteral administration or for administration directly into the liver.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an effective amount", or "therapeutic amount" is indicated, the precise amount of the compositions of the present invention to be administered can be determined by a physician with consideration of individual differences in age, weight, disease, extent of infection or liver damage, and condition of the patient (subject). In certain embodiments, a pharmaceutical composition comprising the cells described herein may be administered at a dosage of $10^3$ to $10^7$ cells/kg body weight and in certain embodiments, $10^5$ to $10^6$ cells/kg body weight, including all integer values within those ranges. The cell compositions may also be administered multiple times at these dosages. The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by injection, transfusion, implantation or transplantation. The compositions described herein may be administered to a patient subcutaneously, intradermally, intratumorally, intranodally, intramedullary, intramuscularly, by intravenous (i.v.) injection, or intraperitoneally.

The cell compositions of the present invention may also be administered using any number of matrices. Matrices have been utilized for a number of years within the context of tissue engineering. The present invention utilizes such matrices within the novel context of acting as an artificial support, maintain, or modulate β islet function. Accordingly, the present invention can utilize those matrix compositions and formulations which have demonstrated utility in tissue engineering.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In certain embodiments of the present invention, the cell compositions of the present invention are administered to an individual in conjunction with (e.g. before, simultaneously or following) any number of relevant treatment modalities, including but not limited to treatment with agents such as antiviral agents, chemotherapy, radiation, immunosuppressive agents, such as cyclosporin, azathioprine, methotrexate, and mycophenolate.

Example I

Differentiation of Hepatic Stem Cells into Insulin-Producing Pancreatic Cells

This example describes the differentiation of human hepatic stem cells into pancreatic β islet-like cells.

Fetal stem cells were mechanically dissociated from a mixed population of whole liver cells using StemPro® EZPassage™ Tool from Invitrogen. The stem cells were pooled and distributed on collagen I coated 12-well dishes. The cells were allowed to attach overnight before inducing differentiation. More specifically, cells were seeded on 0.1% collagen I coated tissue culture plates at a density of 2.0-3.0×10$^6$ cells/plate and allowed to adhere overnight. Cells were then treated for two days in pre-induction media consisting of: Serum Free Iscove's Modified Dulbecco's Medium (IMDM), 2 mmol/L sodium butyrate, and Pen/Strep. Differentiation was accomplished by culturing the cells for at least 24 hours in differentiation media containing: IMDM, 2% KSR, and Pen/Strep. Media was changed every three days and differentiation was assessed in a temporal manner (i.e., at 1, 2, and 3 days).

Cell lysates were isolated 1 or 3 days after induction of differentiation. cDNA was prepared from these lysates in order to screen for the expression of pancreatic-specific genes. Pdx-1 and somatostatin expression was detected at day 3 (FIG. 1, lanes 1 and 4, respectively). Cell grown in Kubota's expansion media alone (control) did not express Pdx-1 or somatostatin. Glut-2 however was expressed (lane5), which indicates that Glut-2 is expressed in hepatic stem cells as well as pancreatic cells.

Example II

Differentiation of HUMCs into Insulin-Producing Pancreatic Cells

This example describes the differentiation of human umbilical cord matrix stem cells into pancreatic p islet-like cells.

Preparation of umbilical cord: Umbilical cords were, weighed, measured, and washed thoroughly 2× for 5 minutes in cold sterile PBS (500 mL). The cord was then washed again in (500 mL) betadine solution 1× for 5 minutes followed by rinsing thoroughly 2× for 5 minutes with cold sterile PBS (500 mL) to remove the betadine. The clamped end of the cord was then removed with a surgical blade within ½-1 inch beyond clamped area. Blood was drained and the blood vessels subsequently flushed with VIAS-PAN® to remove any blood/clots using a large gauge needle and 50 mL syringe.

Isolation of cord matrix cells: The opposite end of the cord was clamped with a sterile Hoffman clamp, and a 3-way luer-lock was placed on the on the needle/cannula end. A syringe with collogenase solution (0.3-1%) was then attached to the 3-way lock and the solution applied for a period until the umbilical cord became moderately swollen. Then, the cord was incubated in a humidified 37° C., 5% $CO_2$ incubator for 0.5 to 3 hours depending upon concentration of collagenase solution (i.e., the greater the concentration of enzyme solution, the shorter the time to complete digestion). "Collagenase solution" can include one or more of the following: Collagenase (0.3-1.0%); Dispase (0.4%-1.0%); Hyaluronidase (0.1-1.0%); DNase (0.03%).

Upon digestion, the Hoffman clamp is removed from the cord and the solution drained into a sterile container. The cord was subsequently flushed with sterile PBS, saving the wash. The cord end was reclamped with a Hoffman clamp, and a solution of hyaluronidase (0.1-1.0%)/DNase (0.3%) applied through the lock for a period until the cord became moderately swollen. Again, the cord was incubated for 1-12 hours. After incubation time, cord and was solution was washed and collected into a sterile container.

Insufficient digestion with cannulation method can be remediated by further digestion in 0.25% hyaluronidase/0.25% collagenase I in digestion buffer for up to 4 hours at 37 C. Tissue is then titurated through 40-60 mesh screen using a cell disassociation sieve.

Cells thus obtained were then depleted of the cells expressing CD31 cells. (CD-31 is a marker commonly expressed on endothelial cells, platelets, macrophages and Kupffer cells, granulocytes, T/NK cells, lymphocytes, megakaryocytes, fibroblasts, osteoclasts, neutrophils, and HUVEC cells). The CD31 depleted suspension of cells were then enriched for CD44 cells. CD44 is a receptor for hyaluronic acid.

Plastic adherent selection: The cell suspension is then plated. 24-48 hours after isolation, non-adherent cells were removed by washing three times with sterile PBS. Fresh DM was added and changed every two days. When culture reached between 50-80% of confluency, the cells were harvested using 0.05% trypsin/0.53 mM EDTA solution and re-plated into a T75 gelatin coated culture flask for further expansion in DM. Cultures were maintained at 50-80% of confluency in a 37° C. humidified incubator with 5% $CO_2$ for propagation.

Differentiation: Prior to induction, cells were seeded on 0.1% collagen I coated tissue culture plates at a density of $2.0-3.0\times10^6$ cells/plate and allowed to adhere overnight. Cells were then treated for two days in pre-induction media consisting of: Serum Free Iscove's Modified Dulbecco's Medium (IMDM), 2 mmol/L sodium butyrate, and Pen/Strep. Differentiation was accomplished by culturing the cells for at least 24 hours in differentiation media containing: IMDM, 2% KSR, and Pen/Strep. Media was change every three days and differentiation was assessed in a temporal manner (i.e., at 1, 2, and 3 days).

Figure 2:
FIG. 2 shows immunohistological staining of insulin production from human UCM cells that have been differentiated into pancreatic β islet-like cells in accordance with the present invention. Brown (dark) staining indicates the presence of insulin. (10× magnification)

Differentiation of the cells was assessed as follows:

Immunocytochemistry. Differentiated cells were fixed with 4% paraformaldehyde in PBS for 10 min and then washed in PBS. Cells were permeabilized with 0.2% Triton X-100 in PBS for 5 min, washed and then blocked in 0.2% Triton X-100, 2% normal serum in PBS for 1 h, and then incubated with antibodies to insulin. After washing three times with PBS, cells were incubated with secondary antibody. The dark staining of the round-shaped cells in FIG. 2 is indicative of insulin expression in those cells. Undifferentiated UCM cells do not stain with anti-human insulin.

Figure 3:
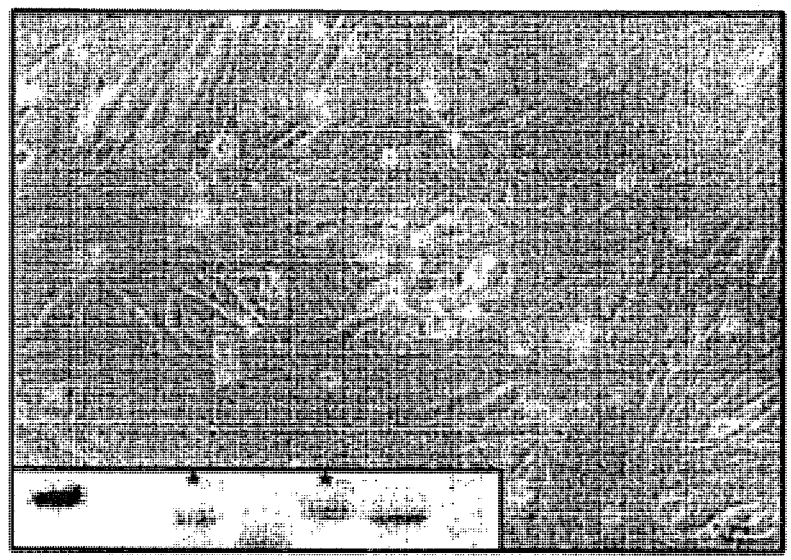
FIG. 3 provides the results of a PCR analysis of cDNA taken from human UCM cells that have been differentiated into pancreatic β islet-like cells in accordance with the present invention. From left to right: lane 1—Pdx-1; lane 2—glucagon; lane 3—insulin; lane 4—glut 2; lane 5—somatostatin; lane 6—GAPDH (control).

RNA isolation and Reverse Transcription Polymerase Chain Reaction (RT-PCR.): RNA was isolated from cells on RNeasy Quick spin columns and converted to cDNA using random hexamers and SuperScript II reverse transcriptase. PCR products were resolved by 2% agarose gel electrophoresis and visualized by ethidium bromide staining. Expression of numerous pancreatic islet β cell-specific genes was analyzed, including Pdx-1, insulin, glucagon, somatostatin, glut2, and GADPH (cDNA loading control). See FIG. 3.

Figure 4:
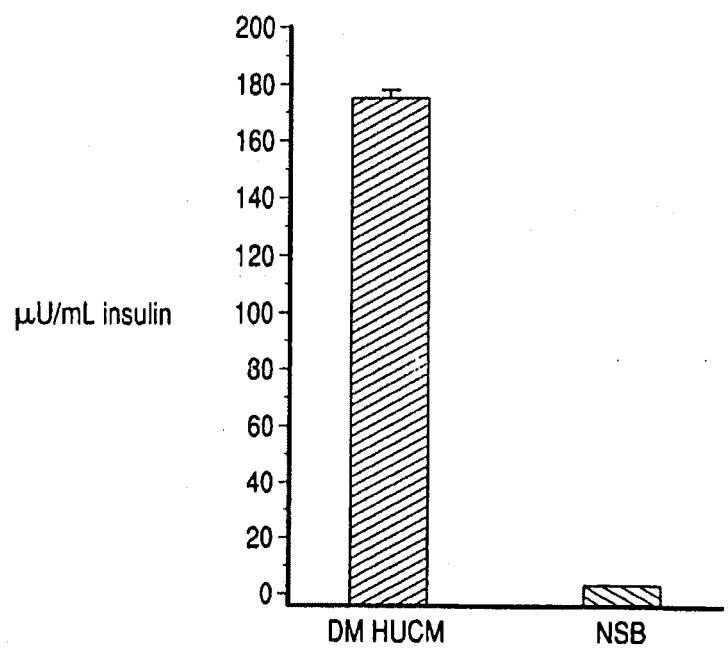
FIG. 4 is a graph showing the amount of insulin secreted into the media (day 5) by human UCM cells that have been differentiated into pancreatic β islet-like cells in accordance with the present invention. NSB: Non-specific binding (control)

Cellular secretion of insulin: The concentration of insulin the culture media was determined by ELISA as described above. See FIG. 4.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method for differentiating progenitor cells into insulin-producing pancreatic cells, comprising:
   (a) incubating the progenitor cells in serum-free pre-induction media comprising a histone deacetylase inhibitor (HDACI); and, subsequently,
   (b) incubating the progenitor cell in induction media comprising knock-out replacement serum;
   for a time sufficient to differentiate the progenitor cells into insulin producing pancreatic cells
   wherein the progenitor cells are selected from the group consisting of hepatic stem cells, hepatoblasts, or hepatic committed progenitors.

2. The method according to claim 1 in which the progenitor cells are human progenitor cells.

3. The method according to claim 1 in which the progenitor cells are hepatic stem cells.

4. The method according to claim 1 in which the induction media comprises about 2% knock-out replacement serum.

5. The method according to claim 1 in which the HDACI is sodium butyrate, phenyl butyrate, retinoic acid, valproic acid, APHA Compound 8, Apicidin, (−) Depudecin, Scriptaid, Sirtinol, and Trichostatin.

* * * * *